United States Patent [19]

Heine

[11] 4,196,980
[45] Apr. 8, 1980

[54] OPTHALMOSCOPE EXAMINATION PATTERN HAVING LIGHT TRANSMISSIVE FIXATION POINT

[75] Inventor: Helmut A. Heine, Herrsching, Fed. Rep. of Germany

[73] Assignees: Propper Manufacturing Co., Inc., Long Island City, N.Y.; Heine Optotechnik GmbH & Co. KG, Herrsching, Fed. Rep. of Germany

[21] Appl. No.: 909,986

[22] Filed: May 26, 1978

Related U.S. Application Data

[63] Continuation of Ser. No. 690,252, May 26, 1976, abandoned, which is a continuation of Ser. No. 481,033, Jun. 20, 1974, abandoned.

[51] Int. Cl.² ............................................. A61B 3/12
[52] U.S. Cl. ....................................... 351/13; 351/16
[58] Field of Search .................................. 351/6, 9–12, 351/13, 14, 16

[56] References Cited

U.S. PATENT DOCUMENTS 1,774,832   9/1930   Keeler .................................. 351/12

OTHER PUBLICATIONS

*The Optician*, "A Guide to Ophthalmoscopes," vol. 157, No. 4071, 4/11/69.
*Textbook of Ophthalmology*, vol. II, Dirke-Elder pp. 1178–1179, Dec. 1937.

*Primary Examiner*—Paul A. Sacher
*Attorney, Agent, or Firm*—Amster, Rothstein & Engelberg

[57] ABSTRACT

The present application discloses an examination pattern for use in conjunction with ophthalmoscopes which provides a light transmissive opening at the pattern center to act as a reference point in the examination of the eye.

3 Claims, 3 Drawing Figures

OPTHALMOSCOPE EXAMINATION PATTERN HAVING LIGHT TRANSMISSIVE FIXATION POINT

This is a continuation of Application Ser. No. 690,252 filed May 26, 1976, now abandoned, which was in turn a continuation of Application Ser. No. 481,033 filed June 20, 1974 now abandoned.

The invention concerns an examination pattern for opthalmoscopes.

Ophthalmoscopes for examining the rear of the eye have the capacity of simultaneously illuminating and inspecting the area to be examined. In their usual embodiment, they essentially contain, in their illumination path, as it is called, a light source, a diaphragm, an objective lens, and a deflection mirror, which directs light into the eye under examination. An observation window is located opposite the eye under examination. This makes it possible for the examining physician to make observations over the deflection mirror, or even through this mirror, if it is designed as a semi-transparent mirror.

To merely observe the rear of the eye, a circular homogeneous illumination field is used; the illumination field aperture, whose image is formed at the rear of the eye, correspondingly consists of a circular opening in the opaque diaphragm. For special examinations, for example, for length measurements, for fixation tests, or for investigating level differences, special illumination field apertures are used. These are attached to an aperture wheel together with the circular aperture, so that the currently desired diaphragm can be switched in rapidly and without removing the ophthalmoscope.

For estimating distances along the retina, the diameter of the pupil or of the optic nerve disk at the rear of the eye has hitherto usually been used as a measure. Their diameter fluctuates between 1.5 and 1.9 mm, and is thus relatively constant as far as biological circumstances are concerned. The result of such estimates is given in terms of the number of pupil diameters by which one spot on the retina is separated from another. This estimate becomes a measurement when a measuring pattern in the ophthalmoscope with a definite distance between lines is projected on the retina. Here, the midpoint of the measurement pattern, for example, the intersection of an axis cross, must be easily fixated by the patient. This presupposes that the measurement pattern does not have too much detail and has an easily fixated center. But it has turned out that a simple axis cross, such as used hitherto, does not provide the patient with an unambiguous object for fixation. Furthermore the foveal reflex (reflex at the site of sharpest vision) is masked at the intersection of the coordinates of the axis cross during correct fixation. To this is added that, when using a simple axis cross, it is difficult to set the middle of the axis cross exactly on the middle of the foveal reflex. The same holds true if the macula (the blind spot of the optic nerve exit) is used as reference point instead of the fovea centralis.

Similar difficulties occur during fixation tests, which serve the important task of differentiating between central (foveal) and eccentric (extra foveal) fixation.

Discovery of eccentric fixation is of great significance because it can be the cause for forming weak vision (amblyopia), which can occur in cross-eyed children. The fixation test is performed with a fixation object built into the ophthalmoscope, usually with a star test pattern. The patient sees the test figure with the eye under investigation and fixes it. When it coincides with the foveal reflex, central or foveal fixation exists. Otherwise, such fixation does not exist.

The hitherto familiar fixation objects have the disadvantage that they are imaged on the fovea, and consequently mask just this part, which ought to be observed during the examination. To this is added that even small test patterns do not permit the patient a sufficiently quiescent fixation, which necessarily entails errors in the result of the examination.

The invention is based on the task of creating an examination pattern for ophthalmoscopes which makes it possible for the examining physician to center the pattern precisely on a desired spot at the rear of the eye, which does not itself mask this spot, and which provides a good fixation object for the patient.

This task is solved according to the invention by providing a light transmitting opening at the reference point of the examination pattern, preferably at its center. This opening is preferably circular. The opening should in principle be as small as possible, but should on the other hand permit sound observation of the foveal reflex, or of another spot which may be chosen as retinal reference point, for example, the center of the pupil or the intersection of two blood vessels.

In applying the invention to a measurement pattern, the "midpoint" of the axis cross is a circle, which serves as an unambiguous fixation object for the patient. During correct fixation, the foveal center must be visible within this circle. Obviously, other spots in the retina or in the eye can be chosen as reference points. The main advantage of the measurement pattern according to the invention consists in the fact that the spot chosen as reference point is in no way masked. It furthermore turns out that the circle situated at the origin of the axis cross makes it possible to center the axis cross very precisely with respect to the desired spot.

In applying the invention to a fixation test pattern, for example, a star-shaped test pattern, a circular aperture is preferably provided at its midpoint. This aperture serves as unambiguous fixation object for the patient, and can be centered very precisely at the desired spot, that is, on the fovea, and at the same time makes it possible to observe this spot. The foveal reflex is thus visible without hindrance. Furthermore, the central opening reduces the opaque surface of the test pattern, which substantially reduces the requirements for central resolving power in the case of central inhibition scotoma, and which makes possible a more quiescent fixation. Finally, for the first time, physiological fixation motions (physiological nystagmus) can be well observed and can be differentiated from pathological forms.

The invention will be better appreciated by reference to the following detailed description of presently preferred embodiments thereof when read in conjuction with the appended drawings, wherein:

DETAILED DESCRIPTION OF THE DRAWINGS

Figure 1:
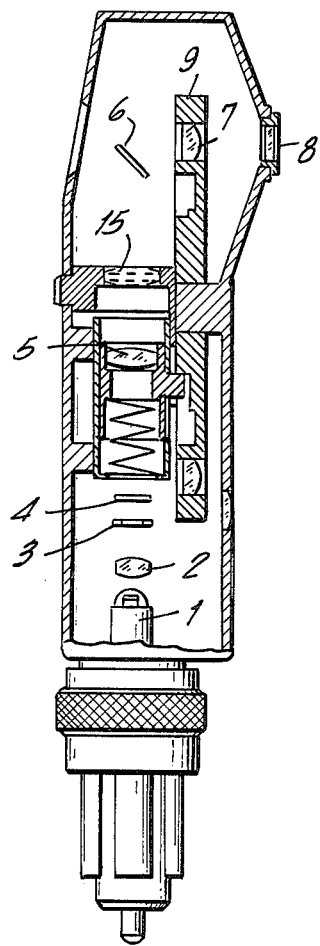
FIG. 1 shows an ophthalmoscope in vertical section.

The ophthalmoscope of the preferred embodiment shown in FIG. 1 is of a type described more fully in my U.S. Pat. No. 3,776,619 and contains an incandescent lamp 1 as light source. This lamp is fed by a battery or by a cable connection (not shown) in a manner known in the art. The illumination field aperture or examination pattern forming mask 3 is illuminated via a condenser 2. Color or polarization filters 4 can be attached at a suitable site in the illumination path.

The illumination objective 5 is mechanically coupled to a lens wheel 9 (rekess disk), and can be moved along the axis of the illuminating beam. It images the apertures or examination patterns, if necessary, via an additional lens 15, at a distance which depends on the focal length of the objective lens 5 and on its distance from the examination pattern forming mask 3. The illuminating beam is deflected by means of mirror 6 towards the eye of the patient. A number of lenses 7 is situated on lens wheel 9. The focal lengths of these lenses differ by suitable steps. Turning the lens wheel allows insertion of the lens with the requisite focal length into the path of the observation beam. The view aperture 8 can be sealed by a plane disk or by a correcting lens.

Figure 2:
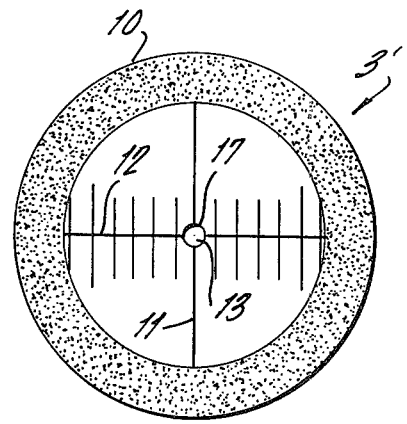
FIG. 2 shows a measurement pattern in accordance with the invention.

FIG. 2 shows a measurement pattern 3', which can be arranged on an aperture wheel, together with the diaphragm and other examination apertures or patterns. The measurement pattern consists of an opaque external ring 10 with an axis cross. The latter consists of a vertical undivided axis 11 and of a horizontal axis 12, which is calibrated. In the center of the axis cross is an inner circle 17, which represents the origin of the axis cross, and which encloses a hole 13. The diameter of the inner circle can, for example, be 0.2 mm, and may correspond to the divisions of the horizontal axis. By turning the axis cross about its midpoint, the measurement axis can be set at any spot at the rear of the eye.

Figure 3:
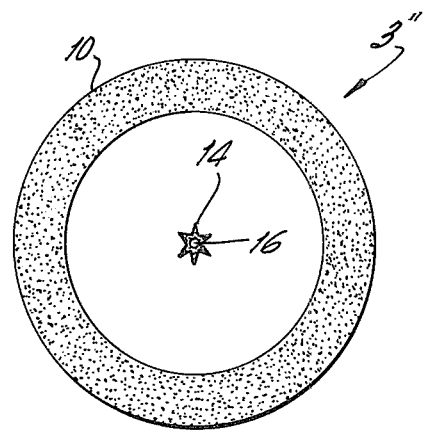
FIG. 3 shows a star-shaped fixation test pattern in accordance with the invention.

FIG. 3 shows an examination pattern with an opaque outer ring 10 and a fixation test pattern 14, in the form of a hexagonal star. The hexagonal star was chosen, because experience shows that children cannot recognize a star in a star figure with four or fewer corners. Furthermore, the child can be made to count the corners of the star, which can give rough information concerning visual capacity. Four corners can be seen as a unit, whereas actual counting begins with more than four corners. A circular hole 16 is provided in the center of the star test figure 14. This hole serves as a fixation object for the patient and allows the star to be centered on the fovea. Its diameter is, for example, 0.06 mm.

What I claim is:

1. An ophthalmoscope comprising means for projecting a beam of light into the eye of a patient and shaping means for forming an examination pattern in said beam for projection onto the retina of said eye, said shaping means including a pattern-forming mask having non-light transmissive portions defining an opaque outer ring and a solid star-shaped figure having at least five points, said star-shaped figure being located at the center of said opaque outer ring, said star-shaped figure having a circular light transmissive opening at the center thereof, the diameter of said light transmissive opening being selected so that the foveal reflex can be visualized through said opening when said star is centered on the fovea.

2. Apparatus in accordance with claim 1 wherein said light transmissive opening has a diameter of approximately 0.06 millemeters.

3. An ophthalmoscope comprising means for projecting a beam of light into the eye of a patient and shaping means for forming an examination pattern in said beam for projection onto the retina of said eye, said shaping means including a pattern-forming mask having non-light transmissive portions defining a pair of perpendicular axes which, when projected on the retina, extend over a substantial portion thereof, at least one of said axes including graduations for comparative measurement of features of said retina, and an open circle at the center of said axes, said axes not extending into said open circle so that said open circle defines a light transmissive space at the center of said axes for observation of features of said retina at said center while making comparative measurements elsewhere on the retina of said eye.

* * * * *